(12) United States Patent
Raupach

(10) Patent No.: US 9,872,662 B2
(45) Date of Patent: Jan. 23, 2018

(54) DETERMINING A SPATIAL DISTRIBUTION OF A MATERIAL PROPERTY VALUE ON THE BASIS OF A SINGLE ENERGY IMAGE RECORDING

(71) Applicant: Siemens Healthcare GmbH, Erlangen (DE)

(72) Inventor: Rainer Raupach, Heroldsbach (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/369,935

(22) Filed: Dec. 6, 2016

(65) Prior Publication Data

US 2017/0172533 A1    Jun. 22, 2017

(30) Foreign Application Priority Data

Dec. 16, 2015 (DE) .................. 10 2015 225 395

(51) Int. Cl.
*A61B 6/00* (2006.01)
*A61B 6/03* (2006.01)

(52) U.S. Cl.
CPC .......... *A61B 6/5217* (2013.01); *A61B 6/032* (2013.01)

(58) Field of Classification Search
CPC ........ A61B 6/032; A61B 6/482; G01V 5/005; G01N 23/046
See application file for complete search history.

(56) References Cited

U.S. PATENT DOCUMENTS

| 2013/0110438 A1* | 5/2013 | Rinkel | G01N 23/087 702/85 |
|---|---|---|---|
| 2014/0328448 A1 | 11/2014 | Wu et al. | |
| 2015/0103971 A1 | 4/2015 | Chen | |

OTHER PUBLICATIONS

Kalendar, et al, Digitale Bilddiagnose: "Materialselektive Bildgebung und Dichtemessung mit der Zwei-Spektren-Methode 1. Grundlagen und Methodik", 7 (1987), pp. 66-72.*
Kalendar, et al, English Machine translation.*

(Continued)

*Primary Examiner* — Edward Park
(74) *Attorney, Agent, or Firm* — Harness, Dickey & Pierce, P.L.C.

(57) ABSTRACT

A method is for determining a spatial distribution of a material property value in an examination region of an examination object. According to an embodiment, the method includes capturing measurement projection data; reconstructing image data based upon the captured measurement projection data; estimating a distribution of two basic materials using a threshold value by classifying image points; determining a distribution of the two basic materials based upon the estimated distribution and a general dependency rule; and determining a spatial distribution of the material property value, independent of the measurement energy, based upon the determined distribution and based upon a previously known theoretical relationship between the distribution of the material property value and a distribution of the two basic materials. In addition, a material property distribution determining device is described in one embodiment, and a computer tomography system is also described in another embodiment.

21 Claims, 5 Drawing Sheets

(56) References Cited

OTHER PUBLICATIONS

Szczykutowicz T. et al; "A simple image based method for obtaining electron density and atomic number in dual energy CT"; Proceedings of SPIE; vol. 7961, 79613A; 2011.
Kis Benedek Janos et al: "Single-Energy Material Decomposition Using X-Ray Path Length Estimation"; Comput Assist Tomogr ; vol. 36 No. 6; Nov./Dec. 2012; pp. 768-777; 2012.
Kalender W. et al: "Matertalselektive Bildgebung und Dichtemessung mit der Zwei-Spektren-Methode, I. Grundlagen und Methodik", Bilddiagn. 7, 1987, pp. 66-72, Georg Thieme Verlag;; 1987.
German Office Action for DE 10 2015 225 395.3 dated Sep. 30, 2016.

* cited by examiner

DETERMINING A SPATIAL DISTRIBUTION OF A MATERIAL PROPERTY VALUE ON THE BASIS OF A SINGLE ENERGY IMAGE RECORDING

PRIORITY STATEMENT

The present application hereby claims priority under 35 U.S.C. §119 to German patent application number DE 102015225395.3 filed Dec. 16, 2015, the entire contents of which are hereby incorporated herein by reference.

FIELD

At least one embodiment of the invention generally relates to a method for determining a spatial distribution of a material property value in an examination region of an examination object. At least one embodiment of the invention further generally relates to a material property distribution determining device. At least one embodiment of the invention further generally relates to a computer tomography system.

BACKGROUND

When planning the irradiation of a patient in the context of radiation therapy, radiological data is captured via e.g. CT image recordings so that the radiation dose for the planned irradiation can be established. In particular, it is important to establish radiation doses with a high degree of spatial resolution, in order to destroy only malign tissue in the region to be irradiated and to preserve adjacent and possibly very sensitive regions.

The interactions occurring between radiation and tissue during the irradiation can be divided into primary and secondary effects. The primary effects are the direct interaction of the radiation with the tissue. In the case of irradiation with photons, the interaction is primarily with electrons. If tissue is irradiated with heavy particles, the interaction is mainly with the atomic nuclei. In addition, in the case of the primary processes described above, so much energy is transferred to the electrons during the interaction that these are separated from the molecule and still have enough energy themselves to cause further ionization processes as a secondary effect. Different effects occur during the interaction of electromagnetic radiation with electrons. The Compton effect is dominant when radiation is absorbed in the soft tissue, this consisting mainly of water, whereas the photoelectric effect is dominant in the case of absorption in solid body matter, such as e.g. bone matter.

In order to be able to determine the radiation dose for radiation therapy in advance, it is necessary to know the charge density distribution, i.e. in particular the electron density distribution or the nuclear charge distribution of the material that is present in the region to be examined.

A conventional method for determining electron densities on the basis of CT image data records consists in mapping attenuation values of the CT image data, also referred to as CT values below, onto electron densities using a simple table. However, a very high level of accuracy is not achieved using this method, because when applying polychromatic X-radiation as used in the case of CT image recordings, CT values of the same material in the image are dependent on the size of the examined object in which they are absorbed, and also dependent on the position of the irradiated region in the cross section of the object.

This stems from the fact that, due to the radiation hardening, a near-surface volume element is exposed to a softer radiation than a centrally situated volume element during the mapping. For the same density and the same material, the near-surface volume element is therefore assigned a higher CT value (greater degree of attenuation) than the centrally situated volume element. Due to the different CT values, the near-surface volume element is therefore assigned a higher electron density than the centrally situated volume element. The accuracy of this method is therefore limited even if a calibration is performed very accurately and repetitively in advance using a test body (so-called phantom).

Another way of determining electron densities is based on the CT measurement using two spectra, also known as dual-energy CT, wherein the recorded measurement data is represented in a basic material breakdown. The measurement data divided according to individual materials can then be mapped onto electron densities again. As explained above, the absorption properties of the biologically relevant materials are essentially based on only two different effects, the photoelectric effect and the Compton effect, and therefore a breakdown of the measurement data according to two basic materials, e.g. water and calcium, is sufficient. In this way, the influence of the patient size and the position of a volume element in the body of the patient is reduced for these materials.

However, not all CT devices have the possibility of a dual-energy image recording, and therefore this method has limited availability.

SUMMARY

The inventors have recognized that this presents the problem of developing a precise method for determining the charge density distribution in an examined region of an examination object, which method also functions when using a single-energy CT system for the prerecording.

At least one embodiment is directed to a method for determining a spatial distribution of a material property value in an examination region of an examination object, to a material property distribution determining device, and to a computer tomography system.

According to at least one embodiment of the inventive method for determining a spatial distribution of a material property value in an examination region of an examination object, e.g. a patient, provision is first made for capturing measurement projection data which was generated from the examination region of the examination object using a single-energy CT recording with a defined measurement energy and using a defined measurement projection geometry. A material property relates to material-specific behavior which can be determined independently of the energy that is used for the measuring X-radiation. Such properties relate to the electron density or the nuclear charge number of a material or material mixture, for example. Furthermore, the attenuation coefficient or the absorption property for a predetermined radiation energy are also material properties. A single-energy CT image recording is usually made using polychromatic X-radiation. This comprises a spectral distribution over a specific energy range, or X-rays having different frequencies but only one frequency interval. A defined measurement projection geometry can include e.g. projection lines, in the direction of which measurement projection data is captured. Image data is then reconstructed on the basis of the captured measurement projection data.

At least one embodiment of the inventive material property distribution determining device comprises a projection data capture unit for capturing measurement projection data. It also has an image data reconstruction unit for reconstructing image data on the basis of projection data. In addition, part of the inventive material property distribution determining device is a material distribution estimating unit for determining an estimated distribution of two basic materials, comprising a first and a second basic material in the examination region, by classifying image points according to whether they contain a significant proportion of the second of the two basic materials using a threshold value.

At least one embodiment of the inventive computer tomography system comprises the inventive material property distribution determining device. For example, the material property distribution determining device can be part of a control device for a computer tomography system or an evaluation system which is attached to the computer tomography system.

A largely software-based realization has the advantage that material property distribution determining devices presently in use can also be upgraded easily by means of a software update in order to operate in the inventive manner. To this extent, at least one embodiment of the invention is also achieved by a corresponding computer program product with a computer program which can be loaded directly into a memory device of at least one embodiment of an inventive material property distribution determining device, comprising program segments for executing all steps of at least one embodiment of the inventive method when the computer program is executed in the material property distribution determining device.

In addition to the computer program, such a computer program product may optionally comprise additional elements such as documentation, for example, and/or additional components including hardware components such as e.g. hardware keys (dongles etc.) for use of the software.

For the purpose of transport to the memory device of the material property distribution determining device and/or storage at the material property distribution determining device, it is possible to use a computer-readable medium, e.g. a memory stick, hard disc or other transportable or permanently installed data medium, on which are stored the program segments of the computer program that can be read into and executed by a computer unit of the material property distribution determining device. In addition, the computer unit can have one or more interworking microprocessors or similar, for example.

The dependent claims and the following description each contain particularly advantageous embodiments and developments of the invention. In particular, the claims of one class of claim can be developed in a similar manner to the dependent claims of another class of claim in this case. Moreover, the various features of different example embodiments and claims can also be combined to form new example embodiments in the context of the invention.

BRIEF DESCRIPTION OF THE DRAWINGS

The invention is explained again in greater detail below on the basis of example embodiments and with reference to the appended figures, in which.

DETAILED DESCRIPTION OF THE EXAMPLE EMBODIMENTS

Figure 1:
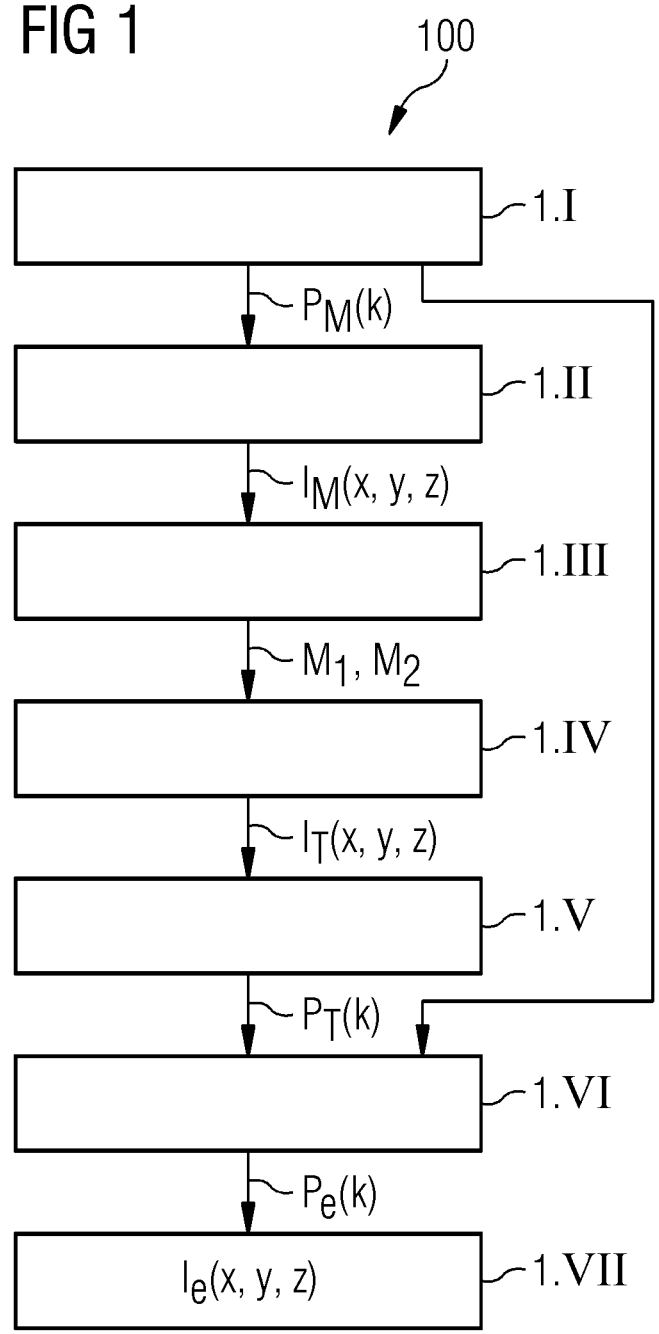
FIG. 1 shows a flow diagram which illustrates a method for determining a spatial distribution of a material property value according to a first example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to at least one embodiment of the inventive method for determining a spatial distribution of a material property value in an examination region of an examination object, e.g. a patient, provision is first made for capturing measurement projection data which was generated from the examination region of the examination object using a single-energy CT recording with a defined measurement energy and using a defined measurement projection geometry. A material property relates to material-specific behavior which can be determined independently of the energy that is used for the measuring X-radiation. Such properties relate to the electron density or the nuclear charge number of a material or material mixture, for example. Furthermore, the attenuation coefficient or the absorption property for a predetermined radiation energy are also material properties. A single-energy CT image recording is usually made using polychromatic X-radiation. This comprises a spectral distribution over a specific energy range, or X-rays having different frequencies but only one frequency interval. A defined measurement projection geometry can include e.g. projection lines, in the direction of which measurement projection data is captured. Image data is then reconstructed on the basis of the captured measurement projection data.

Following thereupon, a distribution of two basic materials comprising a first and a second basic material in the examination region is estimated using a threshold value by classifying image points, preferably in the image data space, according to whether they contain a significant proportion of the second of the two basic materials. Such a distribution can be a 2-material system, for example, which comprises two basic materials.

In a further step, a distribution of the two basic materials is determined on the basis of the estimated distribution and a general dependency rule that has been determined in relation to the dependency of the measurement projection data on a distribution of the two basic materials. The general dependency rule specifies a functional relationship between the distribution of the two basic materials and the values of the measurement projection data. It can be applied experimentally or mathematically, for example, using the same defined measurement projection geometry that was used when recording of the measurement projection data. On the basis of the determined distribution of the two basic materials and a previously known theoretical relationship between the distribution of the material property value and a distribution of the two basic materials, a spatial distribution of the material property value is then determined which is independent of the measurement energy.

Using at least one embodiment of the inventive method, it is therefore possible to determine a material property distribution, in particular an electron density distribution, in an examination region of an examined object, e.g. a patient, using a simple single-energy CT device. Given the knowledge of a material property distribution, it is then possible to plan and carry out therapeutic measures such as an irradiation of tumors, for example. It is therefore advantageously possible to do without sophisticated dual-energy CT systems, such that therapy planning can also take place using simple or older CT systems, even in smaller treatment facilities which are not able to afford these more expensive dual-energy CT systems, and even decentrally. The material property distribution is nonetheless determined with a high degree of accuracy in this case, corresponding to the precision achieved when using sophisticated dual-energy CT systems.

At least one embodiment of the inventive material property distribution determining device comprises a projection data capture unit for capturing measurement projection data. It also has an image data reconstruction unit for reconstructing image data on the basis of projection data. In addition, part of the inventive material property distribution determining device is a material distribution estimating unit for determining an estimated distribution of two basic materials, comprising a first and a second basic material in the examination region, by classifying image points according to whether they contain a significant proportion of the second of the two basic materials using a threshold value.

At least one embodiment of the inventive material property distribution determining device also comprises a basic material distribution determining unit for determining a distribution of the two basic materials on the basis of the estimated distribution and a general dependency rule that has been determined in relation to the dependency of the captured measurement projection data on a distribution of the two basic materials. In addition to this, the inventive material property distribution determining device has a material property distribution determining unit for determining a spatial distribution of the material property value, the distribution being independent of the measurement energy, on the basis of the distribution of the two basic materials and a previously known theoretical relationship between the distribution of the material property value and a distribution of the two basic materials. The additional units of at least one embodiment of the inventive material property distribution determining device comprise evaluation devices which can easily be added to conventional CT imaging systems without having to fundamentally change the existing technical structural units. Therefore the inventive material property distribution determining device can be implemented easily and economically.

At least one embodiment of the inventive computer tomography system comprises the inventive material property distribution determining device. For example, the material property distribution determining device can be part of a control device for a computer tomography system or an evaluation system which is attached to the computer tomography system.

The components of the inventive material property distribution determining device can largely be designed in the form of software components. This relates in particular to parts of the image data reconstruction unit, the material distribution estimating unit, the basic material distribution determining unit and the material property distribution determining unit. In principle, however, some of these components can also be realized in the form of software-supported hardware, e.g. FPGAs or similar, particularly when especially rapid calculations are involved. Likewise, the required interfaces can be designed as software interfaces, e.g. if they only receive data from other software components. However, they can also be designed as hardware-based interfaces which are activated by suitable software.

A largely software-based realization has the advantage that material property distribution determining devices presently in use can also be upgraded easily by means of a software update in order to operate in the inventive manner. To this extent, at least one embodiment of the invention is also achieved by a corresponding computer program product with a computer program which can be loaded directly into a memory device of at least one embodiment of an inventive material property distribution determining device, comprising program segments for executing all steps of at least one embodiment of the inventive method when the computer program is executed in the material property distribution determining device.

In addition to the computer program, such a computer program product may optionally comprise additional elements such as documentation, for example, and/or additional components including hardware components such as e.g. hardware keys (dongles etc.) for use of the software.

For the purpose of transport to the memory device of the material property distribution determining device and/or storage at the material property distribution determining device, it is possible to use a computer-readable medium, e.g. a memory stick, hard disc or other transportable or permanently installed data medium, on which are stored the program segments of the computer program that can be read into and executed by a computer unit of the material property distribution determining device. In addition, the computer unit can have one or more interworking microprocessors or similar, for example.

In an embodiment of the inventive method for determining a spatial distribution of a material property value in an examination region of an examination object, the general dependency rule is determined using a further measurement or a simulation of a measurement signal attenuation depending on a thickness of the two basic materials in the defined measurement projection geometry. For example, the general dependency rule can comprise a function of the signal attenuation depending on the thicknesses of both basic materials in a projection direction in each case. In this context, thickness is understood to be the proportion of one of the two materials in a projection direction. If a projection line having a specific path length runs through the examination region, this path length can be divided into two partial sections which correspond to the thicknesses of the two materials. In other words, along the path, there are sections at which the one material occurs and sections at which the other material occurs. If the sections (or their lengths) assigned respectively to the individual materials are added together, this produces the respective thicknesses of the materials in a projection direction.

The specific thicknesses actually present in the examination region can then be estimated with reference to the measured measurement projection data and on the basis of the estimated distribution of the basic materials. Therefore the estimation of the thicknesses does not take place solely with the aid of the basic material distribution that is estimated on the basis of the captured projection measurement data, but also taking into consideration a functional dependency of the signal attenuation on the values of the thicknesses, wherein the functional dependency can in principle be known to any degree of precision.

It is then possible, knowing the thicknesses of the basic materials and using a previously known theoretical relationship between the distribution of the material property value and the thicknesses of the basic materials, on the basis of the determined thicknesses of the basic materials to determine a spatial distribution of the material property value, e.g. an electron density, which is independent of the measurement energy. Such a procedural approach allows material property values to be determined with distinctly greater precision than would be the case using a simple estimation of the thicknesses of the basic materials based solely on the estimated distribution of the basic materials.

In a preferred embodiment of the inventive method for determining a spatial distribution of a material property value in an examination region of an examination object, the general dependency rule comprises a projection which gives the line integrals of a measurement signal attenuation depending on a distribution of the two basic materials. In this case, measurement signal attenuation is understood to be the attenuation of the X-radiation that is attenuated by the materials present in the examination region. The line integrals run along the projection lines of the defined measurement projection geometry and, along a projection line in the examination region, integrate the signal attenuation that occurs locally along the projection line.

In at least one embodiment of the inventive method for determining a spatial distribution of a material property value in an examination region of a examination object, the previously known theoretical relationship between the distribution of the material property value and a distribution of the two basic materials preferably has a previously known theoretical projection, which gives line integrals of the density of material property carriers, e.g. electrons, contained in the two materials depending on a distribution of the two basic materials. For example, such a theoretical projection reflects the line integral over the material property value, e.g. an electron density, for known thicknesses of the basic materials penetrated by radiation.

In at least one embodiment of the inventive method for determining a spatial distribution of a material property value in an examination region of an examination object, the previously known theoretical relationship between the distribution of the material property value and a distribution of the two basic materials is most preferably formulated as a linear relationship. This linear relationship comprises a sum of the products of the distribution of the two basic materials and the specific densities $\rho 1$, $\rho 2$ of material property carriers contained in the two basic materials. In other words, the theoretical relationship P depending on thicknesses $d1$, $d2$, of the two basic materials can be formulated as follows:

$$P(d_1, d_2) = \rho_1 \cdot d_1 + \rho_2 \cdot d_2. \quad (1)$$

In a particularly advantageous variant of at least one embodiment of the inventive method for determining a spatial distribution of a material property value in an examination region of an examination object, the material property values comprise values relating to the spectral absorption and/or the electron density and/or the nuclear charge carrier density. Using the values relating to the electron density, e.g. irradiation with photons can be planned. With knowledge of the nuclear charge density, treatment methods can be planned in which irradiation with heavy particles such as e.g. protons takes place.

In a particularly advantageous embodiment of the inventive method for determining a spatial distribution of a material property value in an examination region of an examination object, the estimated distribution is determined on the basis of the reconstructed image data with the assumption that the estimated distribution in those subregions of the examination region which contain a significant proportion of the second of the two basic materials is proportionate to the attenuation values of the reconstructed image data. In other words, a linear relationship is assumed between the measured attenuation and the proportion of the second basic material.

In the context of a preferred variant of at least one embodiment of the inventive method for determining a spatial distribution of a material property value in an examination region of an examination object, a synthetic projection data record is determined on the basis of the estimated distribution using a forward projection (in the same geometry as the captured projection data). The projection into the measurement data space allows or aids the subsequent determination of the thicknesses while applying the general dependency rule relating to the dependency of the values of the measurement projection data on a distribution of the two basic materials.

In a particularly practical variant of at least one embodiment of the inventive method for determining a spatial distribution of a material property value in an examination region of an examination object, a reconstruction of image data is performed on the basis of projection values determined by the previously known theoretical projection, in order to determine a spatial distribution of the material property value, the spatial distribution being independent of the measurement energy. The determined projection values give line integrals over the spatial distribution of the material property value. In order to obtain a spatial distribution of the material property value, the projection values must be mapped into the image data space. A filtered back projection is usually performed for this purpose.

In a specific variant of at least one embodiment of the inventive method for determining a spatial distribution of a material property value in an examination region of an examination object, the previously known theoretical relationship between a distribution of the material property value and a distribution of the two basic materials is present in the form of tabulated values of the function depending on the values of the captured measurement projection data and the synthetic projection data. On the basis of the captured measurement projection data and the synthetic projection data that was determined with the aid of an estimation, a tabulated value of the function can be read off directly using a table. This value can be a projection value, for example, which gives line integrals over the spatial distribution of the material property value. From this projection value, it is then possible to calculate a distribution of the required material properties by means of back projection into the image data space.

In order to determine a value of the function of the previously known theoretical relationship between the distribution of the material property value and the distribution of the two basic materials, provision is preferably made for performing an interpolation between two tabulated interpolation nodes. Such a procedural approach allows greater precision if the values of the captured measurement projection data and the estimated synthetic projection data lie between the values of two table entries. Since the projection value to be determined is dependent on two values, i.e. the measurement projection data and the estimated synthetic projection data, it is particularly effective to perform a bilinear interpolation in view of the desired degree of accuracy. However, it is also fundamentally possible to perform non-linear interpolations or a linear interpolation on the basis of only one of the two input values.

FIG. 1 shows a flow diagram 100 which illustrates a method for determining a spatial distribution of a material property value, in this case an electron density distribution, according to a first example embodiment of the invention. In the step 1.I, provision is first made for capturing single-energy CT projection data $P_M(k)$. The data can be recorded in a single-energy CT image recording, for example, directly from an examination region of an examination object. In this case, a CT imaging system is used to record measurement projection data of the examination region from various directions or angles. The index k is intended to represent in simplified form all existing degrees of freedom of the measurement projection data $P_M(k)$. These degrees of freedom include inter alia the projection angle from which the measurement projection data $P_M(k)$ was recorded in each case, the channel number of the detector channel via which the measurement projection data $P_M(k)$ was forwarded, and the detector row of the detector by means of which the measurement projection data $P_M(k)$ was recorded.

In the step 1.II, provision is then made for reconstructing a regular image data record $I_M(x, y, z)$ on the basis of the captured measurement projection data $P_M(k)$. Such a reconstruction is performed using e.g. a filtered back projection onto the captured measurement projection data $P_M(k)$. In the step 1.III, provision is now made for defining a two-material system comprising a first material $M_1$ and a second material $M_2$. Both materials $M_1$, $M_2$ are moreover linearly independent in respect of their absorption properties, and volume elements containing a relevant concentration of the second material $M_2$ can be segmented in the image data by means of a threshold value $T_2$. A suitable two-material system for medical applications comprises the materials water as a first material $M_1$ and bone as a second material $M_2$. Due to the calcium content and the consequently greater contribution of the photoelectric effect, bone is linearly independent in this case and can be identified at a relevant proportion by a threshold $T_2=180$ HU in the CT image.

In the step 1.IV, provision is made for calculating a segmented and transformed or synthetic image data record $I_T(x, y, z)$. Between the values $I_T$ of the segmented or synthetic image data record $I_T(x, y, z)$ and the values of the regular CT image data record $I_M(x, y, z)$, a linear relationship applies when $I_M>T_2$, for example, and $I_T=0$ when $I_M<=T_2$:

$$I_T(x, y, z) = \begin{cases} f(I_M(x, y, z)), & I_M(x, y, z) > T_2 \\ 0 & \text{otherwise} \end{cases} \quad (2)$$

Figure 2:
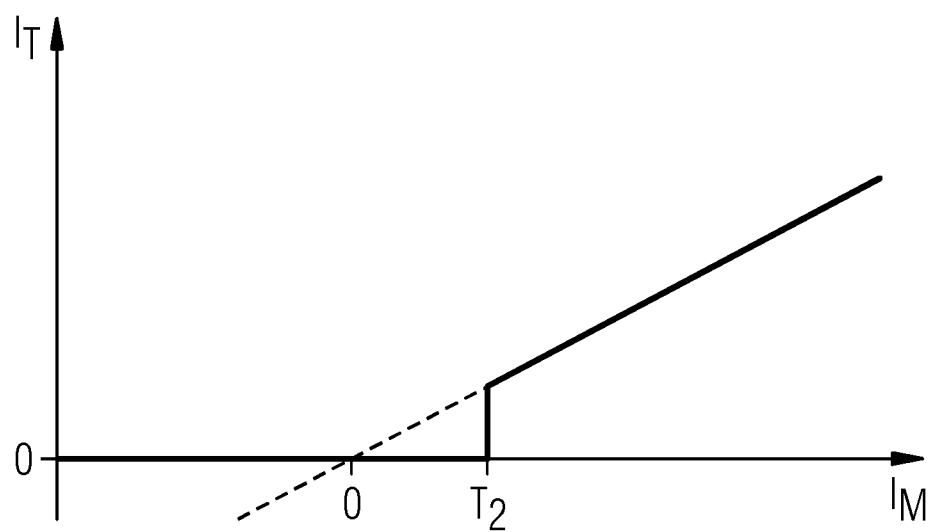
FIG. 2 shows a chart which illustrates a CT values function, the function being applied in the context of the method according to the first example embodiment.

For example $f(t)=a*(t-b)$, wherein e.g. if $I_0$ is set as a value for the attenuation due to water, i.e. using the HU scale, then $b=0$ and $a=\mu2/1000$. The value $\mu2$ here represents the attenuation coefficient of the second material $M_2$. This relationship is illustrated in FIG. 2. The underlying notion is that all volume elements having CT values below the threshold $T_2$ contain only the first material $M_1$ with a variable density, and all volume elements having CT values above the threshold $T_2$ contain the first material $M_1$ and the second material $M_2$ as a mixture, wherein the proportion of the second material $M_2$ increases linearly as the CT value increases in this example embodiment.

In the step 1.V, provision is made for determining a synthetic projection data record $P_T(k)$ on the basis of the calculated segmented synthetic image data record $I_T(x, y, z)$ using a forward projection. The geometry of the applied forward projection in this case corresponds to the geometry of the projection by means of which the captured measurement projection data $P_M(k)$ was generated. In the step 1.VI following thereupon, provision is made for performing a measurement value mapping on the basis of the captured projection data $P_M(k)$ and the synthetic projection data $P_T(k)$ using a function $\Lambda$, wherein projection data $P_e(k)$ is determined as values of the function which most accurately approximate the line integrals of the true charge carrier density in the examination region:

$$P_e(k)=\Lambda(P_M(k), P_T(k)). \quad (3)$$

The mapping can be defined as a function of the thicknesses of both basic materials $P=P(d_1, d_2)$. Assuming that the material thickness of the second material $M_2$ can be determined approximately from the synthetic projection data $P_T$, where $d_2 \approx P_T/\mu_2$, it follows that $P_M \approx P(d_1, P_T/\mu_2)$. On the basis of the strict monotony in the first component $d_1$, this mapping can be inverted such that the unknown thickness $d_1$ of the first material $M_1$ can be determined as $d_1 \approx g(P_M, P_T/\mu_2)$, where the function g is defined implicitly by $P(g(x, y), y)=x$. The line integral over the electron density is known exactly if the thicknesses $d_1, d_2$ penetrated by radiation are known for the basic materials $M_1$, $M_2$:

$$P_e = P_e^{theo}(d_1, d_2) \approx P_e(g(P_M, P_T/\mu_2)). \tag{4}$$

The desired mapping $\Lambda(P_M, P_T)$ is therefore produced from equation 3 and equation 4 as:

$$\Lambda(P_M, P_T) = P_e^{theo}(g(P_M, P_T/\mu_2), P_T/\mu_2). \tag{5}$$

For example, the mapping $\Lambda(P_M, P_T)$ can be calculated in advance and values of the function can be stored in the form of a table depending on the values of the projection data $P_M$, $P_T$ in a database. In the step 1.VI, provision is then made for performing a preferably bilinear interpolation in the form of a two-dimensional lookup between tabulated values in order to obtain the values of the projection data $P_e(k)$.

In the step 1.VII, provision is lastly made for reconstructing a revised CT image data record $I_e(x, y, z)$ on the basis of the determined projection data $P_e(k)$. The revised image data $I_e(x, y, z)$ can either be interpreted directly as physical electron densities, or the electron density is derived in "eHU" relative to water in similar format to the HU values of the CT imaging as:

$$I_e = 1000 \cdot (\rho_e/\rho_e^{H_2O} - 1). \tag{6}$$

In this case, $\rho_e$ specifies the electron density in the material in the examination region and $\rho_e^{H_2O}$ specifies the electron density of water.

Figure 3:
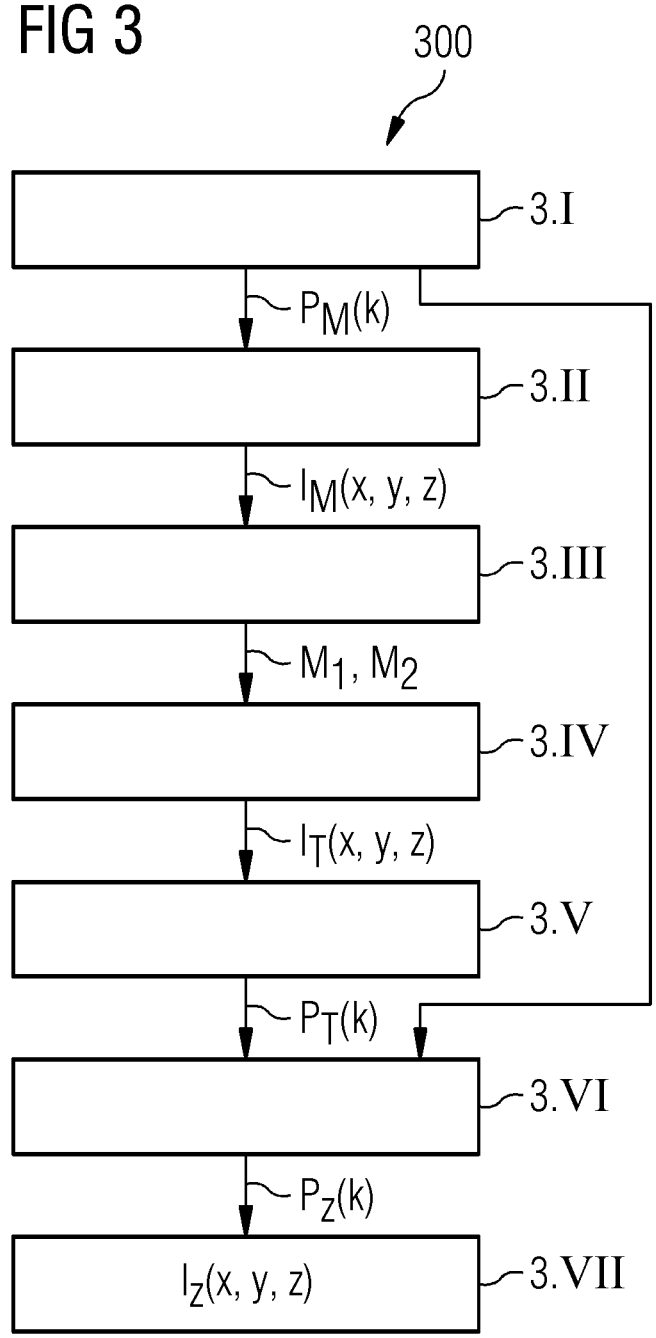
FIG. 3 shows a flow diagram which illustrates a method for determining a spatial distribution of a material property value according to a second example embodiment of the invention.

In the method illustrated in FIG. 3 for determining a spatial distribution of a material property value according to a second example embodiment, provision is made for determining a nuclear charge distribution $I_Z(x, y, z)$. In the case of the second example embodiment, the steps 3.I to 3.V are performed first in a similar manner to the steps 1.I to 1.V illustrated in FIG. 1, and therefore need not be explained again here.

In the step 3.VI, however, provision is then made for performing a measurement value mapping on the basis of the captured projection data $P_M(k)$ and the segmented or synthesized projection data $P_T(k)$ using a different function $\Lambda_z$. Using the function $\Lambda_z$, projection data $P_z(k)$ is determined as values of the function which most accurately approximate the line integrals of the true nuclear charge carrier density in the examination region:

$$P_z(k) = \Lambda_z(P_M(k), P_T(k)). \tag{7}$$

As in the case of the first example embodiment, this mapping can be defined as a function of the thicknesses of both basic materials $P=P(d_1, d_2)$. Assuming that the material thickness can be determined approximately from the segmented projection data $P_T$, where $d_2 \approx P_T/\mu_2$, it follows that $P_M \approx P(d_1, P_T/\mu_2)$. On the basis of the strict monotony in the first component $d_1$, this mapping can be inverted such that the unknown thickness $d_1$ of the first material $M_1$ can be determined as $d_1 \approx g(P_M, P_T/\mu_2)$, where the function g is defined implicitly by $P(g(x, y), y)=x$. The line integral over the nuclear charge density is again known exactly if the thicknesses $d_1, d_2$ penetrated by radiation are known for the basic materials $M_1$, $M_2$:

$$P_z = P_z^{theo}(d_1, d_2) \approx P_z(g(P_M, P_T/\mu_2)). \tag{8}$$

The mapping $\Lambda_z(P_M, P_T)$ is therefore produced from equation 7 and equation 8 as:

$$\Lambda_z(P_M, P_T) = P_z^{theo}(g(P_M, P_T/\mu_2), P_T/\mu_2). \tag{9}$$

For example, the mapping $\Lambda_z(P_M, P_T)$ can be calculated in advance and values of the function can be stored in the form of a table depending on the values of the projection data $P_M$, $P_T$ in a database. In the step 3.VI, provision is then made for performing a preferably bilinear interpolation in the form of a two-dimensional lookup between tabulated values in order to obtain the values for $P_z(k)$.

In the step 3.VII, provision is lastly made for reconstructing a revised CT image data record $I_z(x, y, z)$ on the basis of the determined projection data $P_z(k)$. The revised image data $I_z(x, y, z)$ can either be interpreted directly as physical nuclear charge densities, or the nuclear charge density is derived in "eHU" relative to water in similar format to the HU values of the CT imaging as:

$$I_z = 1000 \cdot (Z/Z^{H_2O} - 1). \tag{10}$$

In this case, Z specifies the distribution of the nuclear charge density in the material mixture present in the examination region, and $Z^{H_2O}$ specifies the nuclear charge density of water.

According to further example embodiments, it is also possible to reconstruct combinations of the electron density $\rho_e$ and the nuclear charge density Z. It is moreover possible on the basis of a single CT measurement separately to determine image data which is assigned to the Compton effect and image data which is assigned to the photoelectric effect. It is additionally possible to determine densities of different materials. It is therefore possible to determine a multiplicity of material property distributions from a single single-energy CT image recording.

Figure 4:
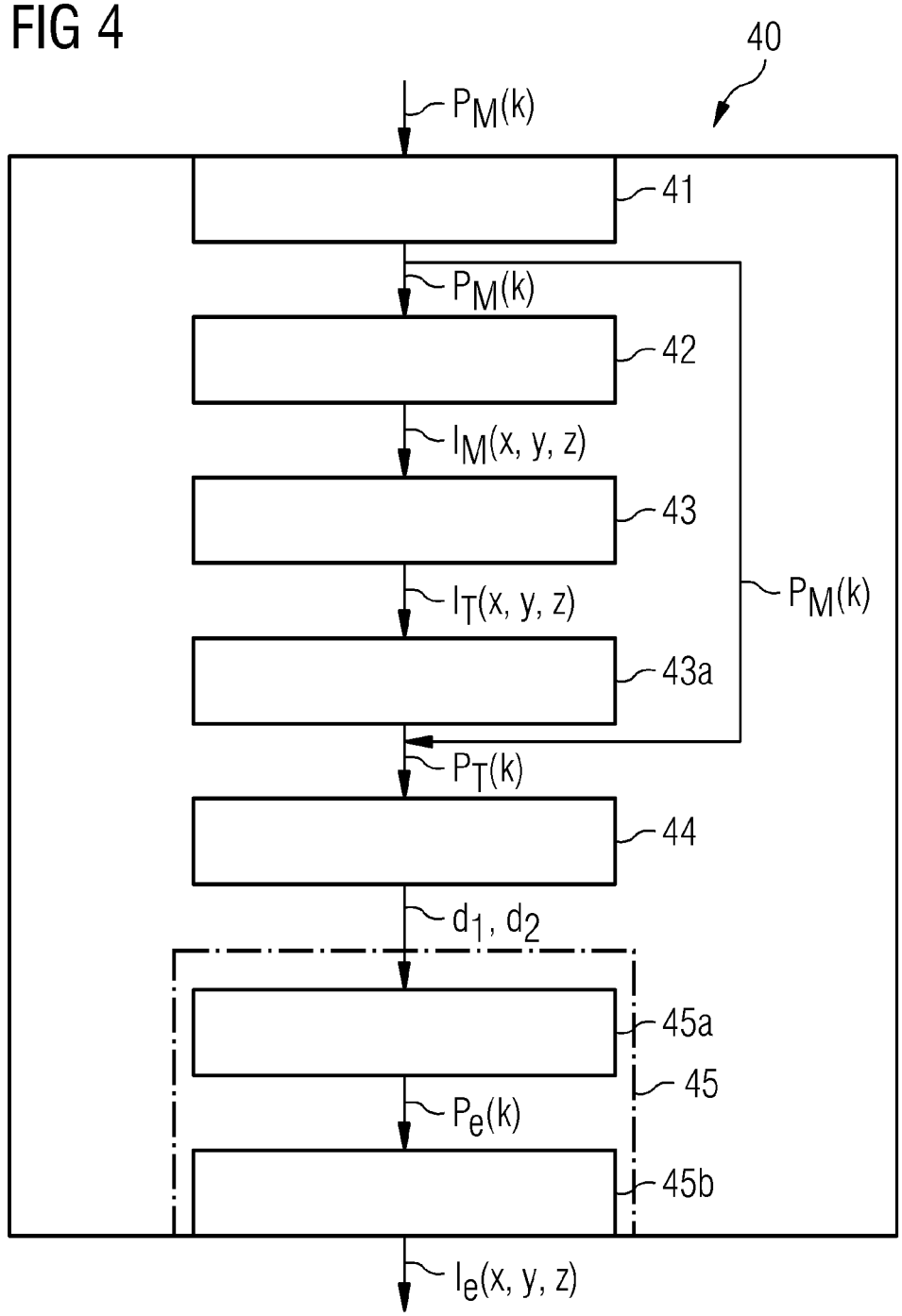
FIG. 4 shows a block schematic diagram which illustrates a material property distribution determining device according to an example embodiment of the invention.

FIG. 4 shows a block schematic diagram which illustrates a material property distribution determining device 40 according to an example embodiment of the invention. The material property distribution determining device 40 comprises a projection data capture unit 41, by means of which measurement projection data $P_M(k)$ is captured. The data can be transferred to the projection data capture unit 41 via an interface (see FIG. 5) to a CT detector, for example. The measurement projection data $P_M(k)$ can also come from a database in which it was stored after imaging of an examination region of an examined object. The captured measurement projection data $P_M(k)$ is then sent to an image data reconstruction unit 42, which reconstructs image data $I_M(x, y, z)$ on the basis of the measurement projection data $P_M(k)$. The image data $I_M$ is then transferred to a material distribution estimating unit 43. The material distribution estimating unit 43 determines an estimated distribution $I_T(x, y, z)$ of two basic materials $M_1$, $M_2$ comprising a first and a second basic material in the examination region FoV by classifying image points according to whether they contain a significant proportion of a second $M_2$ of the two basic materials $M_1$, $M_2$. This is done using a threshold value $T_2$ as explained above with reference to FIG. 1.

The estimated distribution $I_T$ is then forward-projected into the measurement data space in a projection unit 43a, such that synthesized projection data $P_T(k)$ is generated.

The synthesized projection data $P_T(k)$ is then transferred to a basic material distribution determining unit 44, which determines a distribution of the two basic materials $M_1$, $M_2$ on the basis of the determined synthesized projection data $P_T(k)$, the captured measurement projection data $P_M(k)$ and a general dependency rule $P(d_1, d_2)$ that has been determined in relation to the dependency of the captured measurement projection data $P_M$ on a distribution $d_1, d_2$ of the two basic materials $M_1$, $M_2$. For example, the basic material distribution determining unit 44 determines thicknesses $d_1, d_2$ of the two basic materials $M_1$, $M_2$ in the direction of projection lines of the measurement projection data $P_M(k)$. These thicknesses $d_1$, $d_2$ are then forwarded to a material property distribution determining unit 45, which determines a spatial distribution of a material property value $\rho_e$, Z on the basis of the thicknesses $d_1$, $d_2$ of the two materials $M_1$, $M_2$ and on the basis of a previously known theoretical relationship between the distribution of the material property value $\rho_e$, Z and the thicknesses $d_1$, $d_2$ of the two basic materials $M_1$, $M_2$, the spatial distribution being independent of the measurement energy. The material property distribution determining unit 45 comprises a projection data determining unit 45a, which determines projection data $P_e(k)$ that represents a material property distribution in the measurement data space, in the manner described in connection with FIG. 1 and FIG. 3. The determined projection data $P_e(k)$ is then transferred to a back projection unit 45, which is likewise part of the material property distribution determining unit 45 and back-projects the determined projection data $P_e(k)$ into the image data space, such that an image data record $I_e(x, y, z)$ representing a material property distribution is generated.

Figure 5:
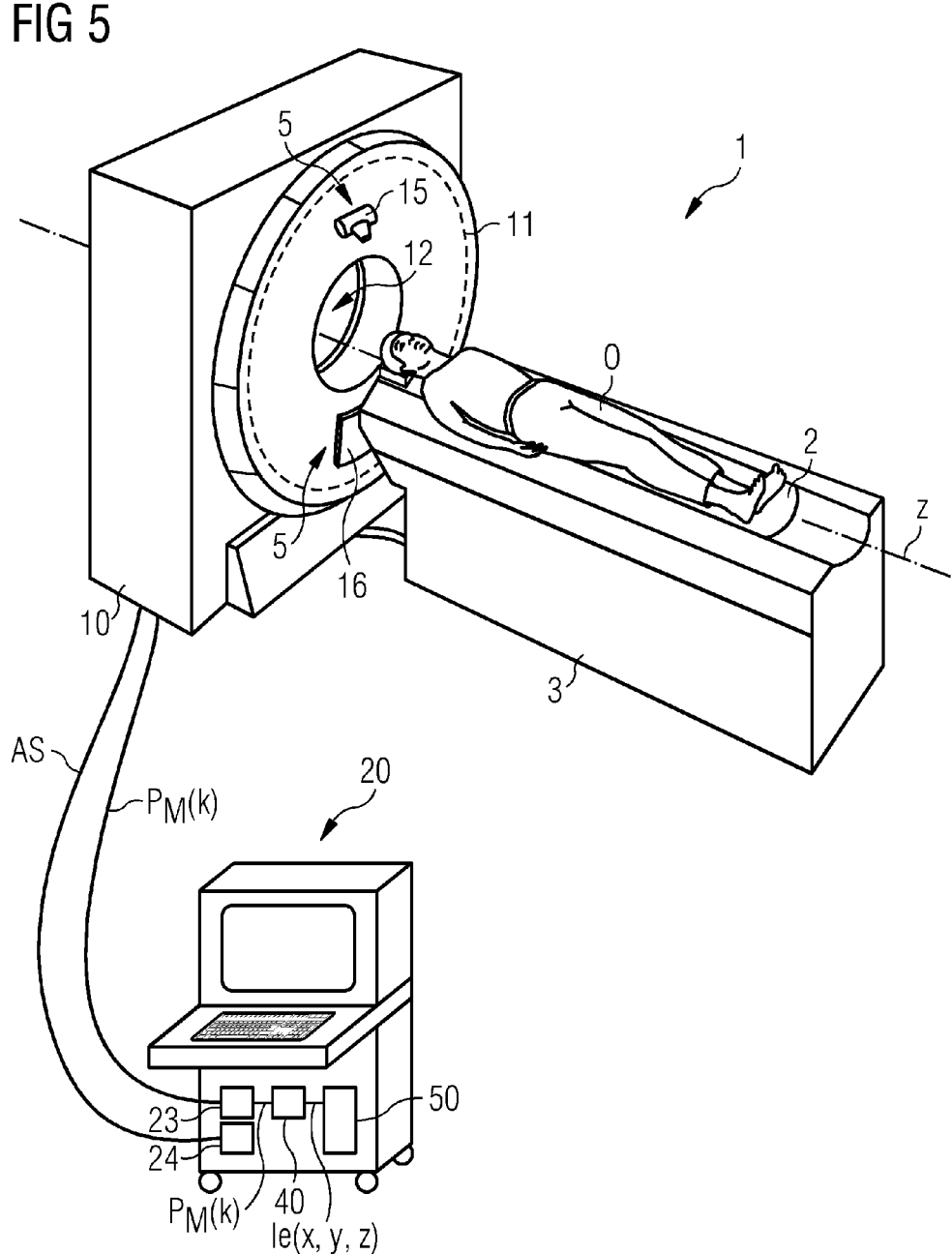
FIG. 5 shows a computer tomography system according to an example embodiment of the invention.

FIG. 5 schematically illustrates a computer tomography system (CT system) 1, with an inventive material distribution determining device 40 according to an example embodiment of the invention.

The CT system 1 in this case consists essentially of a scanner 10, in which a projection data acquisition unit 5 comprising a detector 16 and an X-ray source 15 with is situated opposite the detector 16 rotates about a measurement space 12 on a gantry 11. In front of the scanner 10 is situated a patient support device 3 or patient couch 3, whose upper part 2 and a patient O situated thereon can be pushed towards the scanner 10 in order to move the patient O through the measurement space 12 relative to the detector system 16. The scanner 10 and the patient couch 3 are activated by control device 20, from which acquisition control signals AS are received via a standard interface 24 in order to activate the overall system in accordance with predetermined measurement protocols in the conventional manner. As a result of moving the patient O along the z-direction, this corresponding to the system axis z longitudinally through the measurement space 12, and simultaneously rotating the X-ray source 15, a helical path is produced for the X-ray source 15 relative to the patient O during the measurement. In this case, the detector 16 moves continuously opposite the X-ray source 15 at the same time, in order to capture projection measurement data $P_M(k)$ which is then used to reconstruct volume and/or layer image data. It is likewise possible to perform a sequential measurement method in which a fixed position in a z-direction is selected and the required projection measurement data $P_M(k)$ is then captured during a rotation, a partial rotation or a plurality of rotations at the z-position concerned, in order to reconstruct a sectional image at this z-position or to reconstruct volume image data from the projection data of a plurality of z-positions. In principle, the inventive method can also be used with other CT systems, e.g. with a detector forming a complete ring.

The measurement projection data $P_M(k)$ (also referred to below as raw data) acquired from the detector 16 is transferred via a raw data interface 23 to the control device 20. This raw data then undergoes further processing in a material distribution determining device 40, which can be realized in the form of software on a processor in the control device 20 in this example embodiment. This material distribution determining device 40 determines a material property distribution, e.g. an electron density distribution $I_e(x, y, z)$, on the basis of the raw data $P_M(k)$.

The determined material property distribution is then forwarded to a memory device 50. From there, the information about the material property distribution can be graphically represented on a display screen, for example, or also forwarded to external analysis devices or therapy planning devices (not shown).

In conclusion, it is again noted that the method and devices described above relate only to preferred example embodiments of the invention, and that the invention may be varied by a person skilled in the art without thereby departing from the scope of the invention as specified by the claims. For example, the method for determining a spatial distribution of a material property value in an examination region of an examination object and the material property distribution determining device are explained above primarily with reference to a system for recording medical image data. However, the invention is not limited to an application in the medical field, and can in principle be applied to the recording of image data for other purposes. For the sake of completeness, it is also noted that the use of the indefinite article "a" or "an" does not exclude the possibility of multiple occurrences of the features concerned. Likewise, the term "unit" does not does not exclude the possibility of this comprising a plurality of components, which may also be physically distributed if applicable.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. §112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a spatial distribution of a material property value in an examination region of an examination object, the method comprising:
    capturing measurement projection data for the examination region of the examination object using a single-energy CT recording with a defined measurement energy and using a defined measurement projection geometry;

reconstructing image data based on the measurement projection data;

estimating a distribution of two basic materials, including a first basic material and a second basic material, in the examination region by classifying image points based upon inclusion of a proportion of the second basic material, using a threshold value;

determining a distribution of thicknesses of the two basic materials based on the distribution of two basic materials and a general dependency rule, the general dependency rule determined in relation to dependency of the measurement projection data on the distribution of thicknesses of the two basic materials; and determining the spatial distribution of a material property value based on the distribution of thicknesses of the two basic materials and a previously known theoretical relationship between the spatial distribution of a material property value and the distribution of thicknesses of the two basic materials, the spatial distrubution of a material property value being independent of the defined measurment energy of the single-energy CT recording.

2. The method of claim 1, wherein the general dependency rule is based on a further measurement or a simulation of a measurement signal attenuation depending on the thicknesses of the two basic materials.

3. The method of claim 2, wherein the general dependency rule includes a projection which gives line integrals of a measurement signal attenuation depending on the distribution of thicknesses of the two basic materials.

4. The method of claim 3, wherein the previously known theoretical relationship between the spatial distribution of a material property value and the distribution of thicknesses of the two basic materials includes a previously known theoretical projection, which gives line integrals of a density of material property carriers contained in the two basic materials depending on the distribution of thicknesses of the two basic materials.

5. The method of claim 2, wherein the previously known theoretical relationship between the spatial distribution of a material property value and the distribution of thicknesses of the two basic materials includes a previously known theoretical projection, which gives line integrals of a density of material property carriers contained in the two basic materials depending on the distribution of thicknesses of the two basic materials.

6. The method of claim 2, wherein the spatial distribution of a material property value includes material property values relating to at least one of spectral absorption, electron density and nuclear charge carrier density.

7. The method of claim 1, wherein the general dependency rule includes a projection which gives line integrals of a measurement signal attenuation depending on the distribution of thicknesses of the two basic materials.

8. The method of claim 7, wherein the previously known theoretical relationship between the spatial distribution of a material property value and the distribution of thicknesses of the two basic materials includes a previously known theoretical projection, which gives line integrals of a density of material property carriers contained in the two basic materials depending on the distribution of thicknesses of the two basic material.

9. The method of claim 1, wherein the previously known theoretical relationship between the spatial distribution of a material property value and the distribution of thicknesses of the two basic materials includes a previously known theoretical projection, which gives line integrals of a density of material property carriers contained in the two basic materials depending on the distribution of thicknesses of the two basic materials.

10. The method of claim 9, wherein the determining the spatial distribution of a material property value comprises:

reconstructing further image data based on projection values determined according to the previously known theoretical projection.

11. The method of claim 1, wherein the previously known theoretical relationship between the spatial distribution of a material property value and the distribution of thicknesses of the two basic materials is formulated as a linear relationship including a sum of products of the distribution of the thickness of the two basic materials and a specific density of material property carriers contained in the two basic materials.

12. The method of claim 11, wherein the determining the spatial distribution of a material property value comprises:

reconstructing further data based on projection values determined according to a previously known theoretical projection.

13. The method of claim 1, wherein the spatial distribution of a material property value includes material property values relating to at least one of spectral absorption, electron density and nuclear charge carrier density.

14. The method of claim 1, wherein the estimating a distribution of two basic materials comprises:

estimating the distribution of two basic materials based on the image data and an assumption that the distribution of two basic materials in subregions of the examination region including the proportion of the second basic material is proportional to values of the image data.

15. The method of claim 1, further comprising:

determining a synthetic projection data record based on the distribution of two basic materials using a forward projection.

16. The method of claim 1, wherein the previously known theoretical relationship between the spatial distribution of a material property value and the distribution of thicknesses of the two basic materials is in the form of tabulated values of a function depending on values of the measurement projection data and synthetic projection data, and a value of the function of the previously known theoretical relationship between the spatial distribution of a material property value and the distribution of thicknesses of the two basic materials is determined by performing interpolation between tabulated interpolation nodes.

17. A non-transitory computer-readable medium including computer-readable instructions, which are directly loadable into a memory of a material property distribution determining device, the computer-readable instructions including program segments that, when executed, cause the material property distribution determining device to execute the method of claim 1.

18. A non-transitory computer-readable medium including stored program segments, readable and executable by a processor to execute the method of claim 1 when the program segments are executed by the processor.

19. The method of claim 1, wherein the previously known theoretical relationship between the spatial distribution of a material property value and the distribution of thicknesses of the two basic materials is in the form of tabulated values of a function depending on values of the measurement projection data and synthetic projection data.

20. A material property distribution determining device, comprising:

a memory storing computer-readable instructions; and at least one processor configured to execute the computer-readable instructions to reconstruct image data based on captured measurement projection data for an examination region of an examination object, the captured measurement projection data having been captured using a single-energy CT recording with a defined measurement energy and using a defined measurement projection geometry, estimate a distribution of two basic materials, including a first basic material and a second basic material, in the examination region by classifying image points based upon inclusion of a proportion of the second basic material, using a threshold value determine a distribution of thicknesses of the two basic materials based on the distribution of the two basic materials and a general dependency rule, the general dependency rule determined in relation to the dependency of the captured measurement projection data on the distribution of thicknesses of the two basic materials, and determine a spatial distribution of a material property value based on the distribution of thicknesses of the two basic materials and on a previously known theoretical relationship between the spatial distribution of a material property value and the distribution of thicknesses of the two basic materials, the spatial distribution of a material property value being independent of the defined measurement energy of the single-energy CT recording.

21. A computer tomography system, comprising the material property distribution determining device of claim 20.

\* \* \* \* \*